United States Patent
Heuer et al.

(10) Patent No.: US 6,784,278 B2
(45) Date of Patent: Aug. 31, 2004

(54) POLYCARBONATES, POLYESTER CARBONATES AND POLYESTERS HAVING BRANCHED TERMINAL GROUPS

(75) Inventors: Helmut-Werner Heuer, Krefeld (DE); Rolf Wehrmann, Krefeld (DE); Alexander Meyer, Krefeld (DE); Harald Pielartzik, Krefeld (DE); Friedrich-Karl Bruder, Krefeld (DE); Jos M. J. Paulusse, Eindhoven (NL)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/167,203

(22) Filed: Jun. 11, 2002

(65) Prior Publication Data
US 2003/0096941 A1 May 22, 2003

(30) Foreign Application Priority Data
Jun. 13, 2001 (DE) .......................... 101 28 705

(51) Int. Cl.⁷ .............................................. C08G 64/00
(52) U.S. Cl. ................... 528/196; 264/176.1; 264/219; 528/193; 528/194; 528/198
(58) Field of Search ............................. 264/176.1, 219; 528/193, 194, 196, 198

(56) References Cited

U.S. PATENT DOCUMENTS

| | | | |
|---|---|---|---|
| 3,166,606 A | 1/1965 | Reinking et al. | 260/860 |
| 3,173,891 A | 3/1965 | Fry et al. | 260/47 |
| 4,330,663 A | 5/1982 | Rosenquist | 528/176 |
| 4,929,709 A | 5/1990 | Dujardin et al. | 528/198 |
| 5,043,403 A | 8/1991 | Dujardin et al. | 525/462 |
| 5,106,921 A * | 4/1992 | Maresca | 525/462 |
| 5,783,653 A | 7/1998 | Okamoto | 528/196 |
| 5,959,065 A | 9/1999 | Heuschen et al. | 528/198 |
| 6,140,457 A | 10/2000 | LeGrand et al. | 528/196 |

FOREIGN PATENT DOCUMENTS

| | | |
|---|---|---|
| DE | 41 41 718 | 7/1993 |
| JP | 57-133149 | 8/1982 |
| JP | 6-256499 | 9/1994 |

OTHER PUBLICATIONS

Miller T M et al: "Synthesis of Four Generation Of Monodisperse Aryl Ester Dendrimers Based On 1, 3, 5–Benzenetricarboxylic Acid" Macromolecules, American Chemical Society. Easton, US, Bd. 25, Nr. 12, Jun. 8, 1992, Seiten 3143–3148, XP000269456, ISSN: 0024–9297, Seite 3147, rechte Spalte, Absätze 1, 4, 5 Seite 3148, linke Spalte, Absatz 4 Schema I, III, und IV.

Kunststoff–Hanbuch 3;L. Bottenbruch, Hanser, Munich, (month unavailable) 1992, pp. 127–129 "3.2 Chemischer Aufbau".

* cited by examiner

*Primary Examiner*—Terressa Boykin
(74) *Attorney, Agent, or Firm*—Joseph C. Gil; Aron Preis

(57) ABSTRACT

The use of phenols having a branched structure as terminal groups in polycarbonates, polyester carbonates and polyesters is disclosed. Also disclosed are polycarbonates, polyester carbonates and polyesters having such branched terminal groups, the process for their production and molded parts made therefrom.

4 Claims, No Drawings

POLYCARBONATES, POLYESTER CARBONATES AND POLYESTERS HAVING BRANCHED TERMINAL GROUPS

FIELD OF THE INVENTION

The invention concerns polycarbonates, polyester carbonates and polyesters and more particularly to such polymers having phenols with a branched structure as terminal groups.

SUMMARY OF THE INVENTION

The use of phenols having a branched structure as terminal groups in polycarbonates, polyester carbonates and polyesters is disclosed. Also disclosed are polycarbonates, polyester carbonates and polyesters having such branched terminal groups, the process for their production and molded parts made therefrom.

BACKGROUND OF THE INVENTION

Phenol-based monofunctional terminal groups such as e.g. phenol, 4-alkyl phenols and 4-cumyl phenol are commonly used to produce polycarbonates (Kunststoff-Handbuch 3; L. Bottenbruch, Hanser, Munich 1992, p. 127; EP 0 353 594 A1).

It is not known that these conventionally used terminal groups have a positive influence on flow properties and/or zero shear-rate viscosity and hence on the processing properties of the corresponding polycarbonates.

The production of such polycarbonates having branched terminal groups is known in principle and described for example in EP-A 0 794 209 and JP-A 06 256 499.

For example, p-phenyl phenol is known from U.S. Pat. Nos. 3,166,606 and 3,173,891 as a chain terminator for polycarbonates. Polyester carbonates in which 4-benzyl benzoic acid is used as a chain terminator are known from U.S. Pat. No. 4,330,663 (column 6, line 18).

WO-A 00/50 488 describes the use of di-tert.-alkyl phenol as a chain terminator.

Polycarbonates modified with phenyl propyl phenol, alkyl phenols or naphthol as terminal groups are known from the Japanese laid-open application 57 13 31 49.

Polycarbonates having terminal groups with the structures

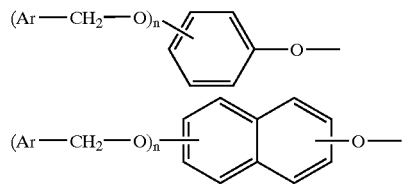

are known from JP-A 06 25 64 99.

According to DE-A 38 03 939, chain terminators having the formula

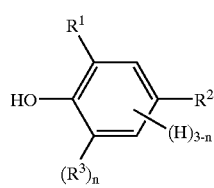

are used, wherein $R^1$, $R^2$, $R^3$ are the same or different and are $C_2$–$C_{12}$ alkyl or $C_8$–$C_{20}$ aralkyl, whereby at least one of the radicals $R^1$ or $R^2$ is a $C_8$–$C_{20}$ aralkyl radical, and wherein "n" has a value between 0.5 and 1.

These known polycarbonates, polyester carbonates and polyesters often have the disadvantage of a high melt viscosity, however.

The present object is therefore to provide polycarbonates, polyester carbonates and polyesters having suitable phenols as terminal groups, which avoid the disadvantage of a high melt viscosity.

DETAILED DESCRIPTION OF THE INVENTION

Surprisingly it was found that this object is achieved by the use of terminal groups having a special branched, in particular dendrimer-type structure. These terminal groups have a positive influence on the melt viscosity, in other words the corresponding polycarbonate displays a lower melt viscosity with a comparable molecular weight distribution and is therefore more readily processable.

Phenolic terminal groups having a dendrimer-type structure based on ester-bridged or ether-bridged aryl systems have not been known until now.

The present invention therefore provides polycarbonates, polyester carbonates and polyesters containing branched, in particular dendrimer-type terminal groups. The invention also concerns the use of the inventive polymeric resins in producing useful articles.

The present invention therefore also provides the use of the phenols according to formula (1) to produce terminal group-modified polymers and the phenols having formula (2)—excluding bis($C_1$–$C_{18}$ alkyl phenyl)-4-hydroxyisophthalates (DE-A 19 62 229), unsubstituted diphenyl hydroxyisophthalate and bis[(diphenyl oxycarbonyl) phenyl] hydroxyisophthalate (T. M. Miller, E. W. Kwock, T. X. Neenan, Macromolecules, 1992, 25, 3143–3148), unsubstituted diphenyl oxyphenol (DE-A 16 44 922), 3,5-dibenzoyl phenol (Dischendorfer et al., Monatsh. Chem. 1935, 66, 255), 4-methyl-2,6-dibenzoyl phenol (S. K. Gupta et al., Transition Met. Chem. 1997, 22, 372–374), 2-methyl-4,6-dibenzoyl phenol (K. C. Amin et al. J. Indian Chem. Soc. 1960, 37, 469–472) and 3,5-bis(4-hydroxybenzoyl) phenol (A. Morikawa, M. Kakimoto, Y. Imai Macromolecules 1993, 26, 6325)—themselves, and the preparation thereof.

The suitable phenols conform to formula (1)

$$\text{HO}\text{—}\text{Ar}_1\text{—}[\text{X}\text{—}\text{Ar}_2]_n \qquad (1)$$

wherein $Ar_1$ and $AR_2$ independently one of the other denote an optionally substituted mononuclear or polynuclear aromatic radical, X is a single bond or a divalent radical, preferably —$CO_2$—, —O—, —$CH_2$— or —CO— and n is 1 to 5.

Preferred phenols conform to formula (2):

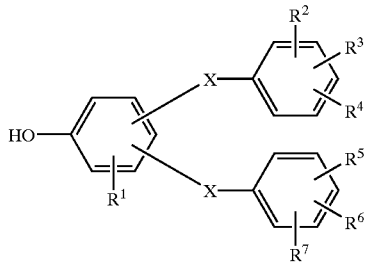

(2)

wherein $R^1$, $R^2$, $R^7$ independently one of the others denote H, linear or branched $C_1$–$C_{18}$ alkyl, Cl, or Br, preferably for H or linear or branched $C_1$–$C_{12}$ alkyl, particularly preferably for H or $C_1$–$C_8$ alkyl and most preferably all denote the same radical, preferably H, X is a single bond or a divalent radical, such as —$CO_2$—, —O—, —$CH_2$— or —CO—, preferably an ester group (2a), an ether group (2b) or a carbonyl group (2c), $R^3$–$R^6$ independently one of the others denote H, linear or branched $C_1$–$C_{18}$ alkyl, cyclic $C_5$–$C_{18}$ alkyl, phenyl, phenyloxy, phenyl carboxy, benzyl, benzyloxy, naphthyl or naphthyloxy, naphthylcarboxy radicals, preferably H, linear or branched $C_1$–$C_{12}$ alkyl, cyclic $C_5$–$C_{12}$ alkyl, phenyloxy, benzyloxy or naphthyloxy radicals and particularly preferred are the embodiments where these denote the same radical, in particular H, linear or branched $C_1$–$C_{12}$ alkyl, cyclic $C_5$–$C_{12}$ alkyl, phenyloxy or benzyloxy radical.

The phenols corresponding to formulae 2a–2c are particularly preferred:

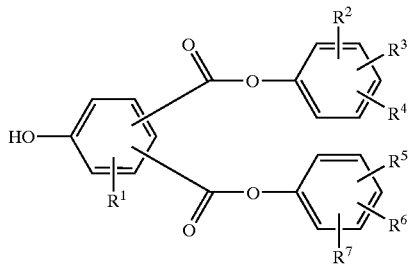

(2a)

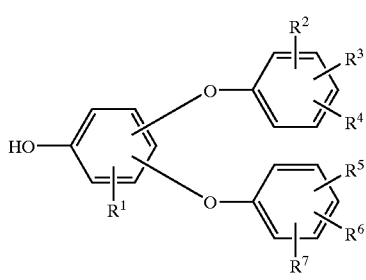

(2b)

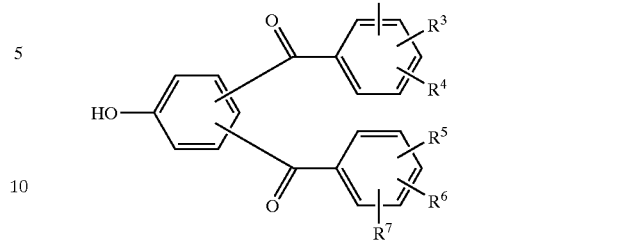

(2c)

wherein 2a to 2c the radicals $R^1$ to $R^7$ have the meanings specified above.

Suitable terminal groups useful for modifying polycarbonates, polyestercarbonates and polyesters are represented by Formula (3):

$$—O—Ar_1—[—X—Ar_2]_n \quad (3)$$

wherein Ar 1, X and Ar2 have the meanings specified above. Preferably suitable are terminal groups according to Formula (3a):

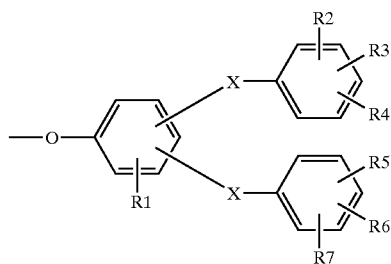

(3a)

wherein X, and R1–R7 have the meanings specified above.

Independently from each other particularly suitable are the terminal groups derived from Phenols of formulas (2a) to (2c).

Preferred, particularly preferred, very particularly preferred or especially preferred or suitable etc. are such compounds, bearing the as preferred, particularly preferred, very particularly preferred or especially preferred or suitable mentioned Substituents.

The radical definitions and explanations cited above in general terms or in preferential ranges may also be combined with one another in any way, in other words the invention embraces any combination of the individual ranges and preferential ranges. Accordingly these apply both to the end products and to the preliminary and intermediate products.

The present invention therefore also provides thermoplastic polycarbonates, thermoplastic polyester carbonates and thermoplastic polyesters with terminal groups derived from the phenols having formulae (1) and (2).

Examples of phenols having formula (1) are 3,5-diphenyl oxyphenol, 3,5-bis(p-tert.-butyl phenyloxy) phenol, 3,5-bis (p-n-butyl phenyloxy) phenol, 1,3-diphenyl-5-hydroxyisophthalate, 1,3-bis(p-tert.-butyl phenyl)-5-hydroxyisophthalate, 1,3-bis(p-iso-octylphenyl)-5-hydroxyisophthalate, 1,3-bis(3,5-di-tert.-butyl phenyl)-5-hydroxyisophthalate, 1,3-bis[p-(2-phenyl prop-2yl) phenyl]-5-hydroxyisophthalate, 1,3-dicyclooctyl-5-hydroxyisophthalate, 1,3-dicyclododecyl-5-hydroxyisophthalate and 1,3-bis[3,5-(diphenyl oxycarbonyl) phenyl]-5-hydroxyisophthalate.

The monophenols having formula (1) for use according to the invention may be produced by methods known from the literature (T. M. Miller, E. W. Kwock, T. X. Neenan, Macromolecules 1992, 25, 3143–3148, A Morikawa, M. Kakimoto, Y. Imai, Macromolecules 1993, 26, 6324–6329). Of the phenols described in the embodiment examples, 1,3-diphenyl-5-hydroxyisophthalate and 1,3-bis[3,5-(diphenyl oxycarbonyl) phenyl]-5-hydroxyisophthalate (T. M. Miller, E. W. Kwock, T. X. Neenan, Macromolecules 1992, 25, 3143–3148) and 3,5-diphenyloxyphenol (DE A 16 44 922) are known. Of phenols having formula (2a), bis ($C_1$–$C_{18}$ alkylphenyl)-4-hydroxyisophthalates are known from DE-A 19 62 229.

In addition to the phenols having formula (1), other phenols in quantities of up to 50 mol % relative to the total quantity of chain terminators in each case may also be used in the production of the polycarbonates, polyester carbonates and polyesters of the invention.

The present invention therefore also provides the use of the phenols having formula (1) optionally in combination with other phenols as chain terminators to produce aromatic polycarbonates, aromatic polyester carbonates and aromatic polyesters, whereby the other phenols are used in quantities of up to 50 mol %, preferably up to 25 mol % relative to the total molecular weight of chain terminators in each case.

The present invention therefore also provides thermoplastic polycarbonates, thermoplastic polyester carbonates and thermoplastic polyesters having the formula (4)

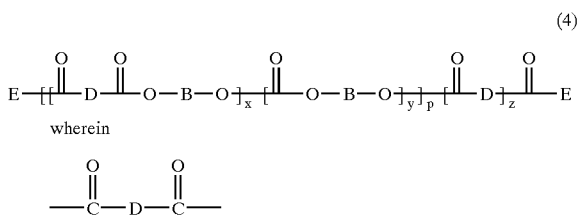

is the radical of an aromatic dicarboxylic acid, —O—B—O— is a bisphenolate radical, "p" is a whole number between 25 and 700, "x" and "y" are fraction numbers consisting of the series o/p, 1/p . . . p/p, whereby x+y=1 and "z" is zero or 1 and at least 50 mol % of the radicals E correspond to phenolate radicals derived from the phenols of formula (1) and a maximum of 50 mol % of the radicals E correspond to a phenolate radical other than those derived from formula (1).

According to DE-A 2 119 799, polycarbonates are produced using phenolic terminal groups by the interfacial polycondensation process and by the method in the homogeneous phase.

On the production of polycarbonates by the interfacial polycondensation process, reference is made by way of example to H. Schnell, Chemistry and Physics of Polycarbonates, Polymer Reviews, Vol. 9, Interscience Publishers, New York 1964 and to Polymer Reviews, Vol. 10, "Condensation Polymers by Interfacial and Solution Methods", Paul W. Morgan, Interscience Publishers, New York 1965, chapter VIII, p. 325.

In addition, the polycarbonates according to the invention may also be produced by the known polycarbonate method in the melt, known as the melt interesterification method, as described for example in WO-A 01/05866 or in WO-A 01/05867. Interesterification methods (acetate method and phenyl ester method) are also described for example in U.S. Pat. Nos. 3,494,885, 4,386,186, 4,661,580, 4,680,371 and 4,680,372, in EP-A 26 120, 26 121, 26 684, 28 030, 39 845, 91 602, 97 970, 79 075, 14 68 87, 15 61 03, 23 49 13 and 24 03 01, and in DE-A 14 95 626 and 22 32 977.

Examples of diarylcarbonates useful in the present invention are diesters of carbonic acid according to formula (5)

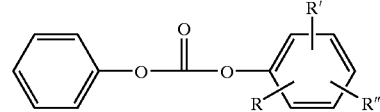

and formula (6),

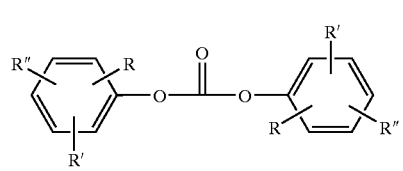

wherein
R, R' and R" independently one of the others denote H, linear or branched $C_1$–$C_{34}$-alkyl, $C_1$–$C_{34}$-cyclic alkyl, $C_7$–$C_{34}$-alkaryl or $C_6$–$C_{34}$-aryl or $C_6$–$C_{34}$-aryl-oxy, for example
diphenylcarbonate, butylphenyl-phenylcarbonate, di-butylphenylcarbonate, isobutylphenyl-phenylcarbonate, di-isobutylphenylcarbonate, tert-butylphenyl-phenylcarbonate, di-tert-butylphenylcarbonate, n-pentylphenyl-phenylcarbonate, di-(n-pentylphenyl)carbonate, n-hexylphenyl-phenylcarbonate, di-(n-hexylphenyl) carbonate, cyclohexylphenyl-phenylcarbonate, di-cyclohexylphenylcarbonate, phenylphenol-phenylcarbonate, di-phenylphenolcarbonate, isooctylphenyl-phenylcarbonate, di-isooctylphenylcarbonate, n-nonylphenyl-phenylcarbonate, di-(n-nonylphenyl)carbonate, cumylphenyl-phenylcarbonate, di-cumylphenylcarbonate, naphthylphenyl-phenylcarbonate, di-naphthylphenylcarbonate, di-tert-butylphenyl-phenylcarbonate, di-(di-tert-butylphenyl) carbonate, dicumylphenyl-phenylcarbonate, di-(dicumylphenyl)carbonate, 4-phenoxyphenyl-phenylcarbonate, di-(4-phenoxyphenyl)carbonate, 3-pentadecylphenyl-phenylcarbonate, di-(3-pentadecylphenyl)carbonate, tritylphenyl-phenylcarbonate, di-tritylphenylcarbonate, preferably
diphenylcarbonate, tert-butylphenyl-phenylcarbonate, di-tert-butylphenylcarbonate, phenylphenol-phenylcarbonate, di-phenylphenolcarbonate, cumylphenyl-phenylcarbonate, di-cumylphenylcarbonate, and particularly preferably for diphenylcarbonate.

Diphenols for polycarbonates of this type may for example be hydroquinone, resorcinol, dihydroxy biphenyls, bis(hydroxyphenyl) alkanes, bis(hydroxyphenyl) cycloalkanes, bis(hydroxyphenyl) sulfides, bis (hydroxyphenyl) ethers, bis(hydroxyphenyl) ketones, bis (hydroxyphenyl) sulfones, bis(hydroxyphenyl) sulfoxides, α,α'-bis(hydroxyphenyl) diisopropyl benzenes, as well as ring-alkylated and ring-halogenated compounds thereof, and also α,ω-bis(hydroxyphenyl) polysiloxanes.

Preferred diphenols are for example 4,4'-dihydroxybiphenyl (DOD), 2,2-bis(4-hydroxyphenyl) propane (bisphenol A), 1,1-bis(4-hydroxyphenyl)-3,3,5-trimethyl cyclohexane (bisphenol TMC), 1,1-bis(4-hydroxyphenyl cyclohexane, 2,4-bis(4-hydroxyphenyl)-2-methyl butane, 1,1-bis(4-hydroxyphenyl)-1-phenyl ethane, 1,1-bis(4-hydroxyphenyl)-p-diisopropyl benzene, 1,3-bis[2-(4-hydroxyphenyl)-2-propyl]benzene (bisphenol M), 2,2-bis(3-methyl-4-hydroxyphenyl) propane, 2,2-bis(3-chloro-4-hydroxyphenyl) propane, bis(3,5-dimethyl-4-hydroxyphenyl) methane, 2,2-bis(3,5-dimethyl-4-hydroxyphenyl) propane, bis(3,5-dimethyl-4-hydroxyphenyl) sulfone, 2,4-bis(3,5-dimethyl-4-hydroxyphenyl)-2-methyl butane, 2,2-bis(3,5-dichloro4-hydroxyphenyl) propane and 2,2-bis(3,5-dibromo-4-hydroxyphenyl) propane.

Particularly preferred diphenols are for example 2,2-bis(4-hydroxyphenyl) propane (bisphenol A), 1,3-bis[2-(4-hydroxyphenyl)-2-propyl] benzene (bisphenol M), 2,2-bis(3,5-dimethyl-4-hydroxyphenyl) propane, 1,1-bis(4-hydroxyphenyl)-1-phenyl ethane, 2,2-bis(3,5-dichloro-4-hydroxyphenyl) propane, 2,2-bis(3,5-dibromo-4-hydroxyphenyl) propane, 1,1-bis(4-hydroxyphenyl) cyclohexane and 1,1-bis(4-hydroxyphenyl)-3,3,5-trimethyl cyclohexane (bisphenol TMC).

The diphenols may be used both alone and in combination with one another and thus yield homopolycarbonates or copolycarbonates. The diphenols are known from the literature or may be produced by methods known from the literature (see e.g. H. J. Buysch et al., Ullmann's Encyclopedia of Industrial Chemistry, VCH, New York, 1991, $5^{th}$ Ed., Vol. 19, p. 348).

Small quantities, preferably quantities of between 0.05 and 2.0 mol %, relative to the moles of the diphenols used, of trifunctional or polyfunctional compounds, in particular those having three or more phenolic hydroxyl groups as so-called branching agents, may also additionally be used. Some of the compounds having three or more phenolic hydroxyl groups that may be used are for example phloroglucinol, 4,6-dimethyl-2,4,6-tri(4-hydroxyphenyl)-hept-2-ene, 4,6-dimethyl-2,4,6-tri(4-hydroxyphenyl) heptane, 1,3,5-tri(4-hydroxyphenyl) benzene, 1,1,1-tri(4-hydroxyphenyl) ethane, tri(4-hydroxyphenyl) phenyl methane, 2,2-bis[4,4-bis(4-hydroxyphenyl) cyclohexyl] propane, 2,4-bis(4-hydroxyphenyl isopropyl) phenol, 2,6-bis(2-hydroxy-5'-methyl benzyl)-4-methyl phenol, 2-(4-hydroxyphenyl)-2-(3,4-dihydroxyphenyl) propane, hexa[4-(4-hydroxyphenyl isopropyl) phenyl] orthoterephthalic acid ester, tetra[4-(4-hydroxyphenyl isopropyl) phenoxy] methane, tetra(4-hydroxyphenyl) methane and 1,4-bis(4',4"-dihydroxytriphenyl) methyl benzene.

Other possible branching agents are 2,4-dihydroxybenzoic acid, trimesic acid, cyanuric chloride and 3,3-bis(3-methyl-4-hydroxyphenyl)-2-oxo-2,3-dihydroindole.

The 0.05 to 2 mol %, relative to diphenols used, of branching agents that may optionally additionally be used may either be introduced into the aqueous alkaline phase together with the diphenols themselves and the molecular weight regulators according to the invention or added prior to phosgenation, dissolved in an organic solvent.

The aromatic polycarbonates according to the present invention have weight-average molecular weights $M_w$ (determined by gel permeation chromatography and calibration with polystyrene standard) of between 5,000 and 200,000, preferably between 10,000 and 80,000 and particularly preferably between 15,000 and 40,000.

The (viscosity number) relative solution viscosities are accordingly between 1.10 and 1.60, measured in methylene chloride (0.5 g polycarbonate in 100 ml methylene chloride at 23° C.).

Polyester carbonates according to the invention are those made up of at least one diphenol, at least one aromatic dicarboxylic acid and carbonic acid.

Suitable aromatic dicarboxylic acids are for example orthophthalic acid, terephthalic acid, isophthalic acid, tert.-butyl isophthalic acid, 3,3'-diphenyl dicarboxylic acid, 4,4'-diphenyl ether dicarboxylic acid, 4,4'-diphenyl sulfone dicarboxylic acid, 3,4'-benzophenone dicarboxylic acid, 2,2-bis(4-carboxyphenyl) propane, trimethyl-3-phenylindane-4,5-dicarboxylic acid.

Of the aromatic dicarboxylic acids, terephthalic acid and/or isophthalic acid are particularly preferably used.

Suitable diphenols are those specified above for polycarbonate production. The carbonic acid may be incorporated into the polyester carbonates either via phosgene or via diphenyl carbonate, depending on which production method is selected, in other words depending on hether interfacial polycondensation or melt interesterification is used for polyester carbonate production.

The same applies to the aromatic dicarboxylic acids; they are either used as aromatic dicarboxylic acid dichlorides in the interfacial polycondensation process or as dicarboxylic acid diesters in the melt interesterification process.

The polyester carbonates according to the invention are produced by known production methods, in other words as already mentioned by the interfacial polycondensation process or by the melt interesterification process.

The polyester carbonates according to the invention may be linear or branched by known means. The aromatic polyester carbonates according to the present invention have average weight-average molecular weights $M_w$ (determined by gel permeation chromatography with polystyrene calibration) preferably between 10,000 and 250,000.

The molar ratio of carbonate units to aromatic dicarboxylate units in the polyester carbonates according to the invention is preferably 95:5 to 5:95 particularly preferably 90:10 to 10:90, very particularly preferably 80:10 to 20:80, especially 60:40 to 40:60, ideally 50:50.

In the case of the polyesters (4) according to the invention "z" is either 0 or 1.

Aromatic polyesters according to the invention are those derived from at least one diphenol and at least one aromatic dicarboxylic acid.

Suitable diphenols and dicarboxylic acids are those cited above for polyester carbonate production.

The aromatic polyesters according to the invention are produced by known production methods (see e.g. Kunststoff-Handbuch, Vol. VIII, p. 695 et seq., Carl-Hanser-Verlag, Munich, 1973).

The aromatic polyesters according to the invention may be linear or they may be branched by known means.

The aromatic polyesters according to the invention have average weight-average molecular weights $M_w$ (determined by the light scattering method) preferably between 25,000 and 70,000; this corresponds to degrees of polymerisation "p" in formula (4) of 80 to 270, whereby "x"=1, "y"=0 and z=1.

The quantity of monophenols according to the invention having formula (1) to be used in producing the polycarbonates, polyester carbonates or polyesters according to the invention is between 0.5 mol % and 8 mol %, preferably between 2 mol % and 6 mol %, relative to the diphenols used in each case.

The conventional monophenols such as for example phenol, 4-alkyl phenols and 4-cumyl phenol are suitable as additional chain terminators.

The present invention therefore also provides a process for the production of the polycarbonates, polyester carbonates or polyesters according to the invention from diphenols, monophenols, carbonic acid derivatives and/or dicarboxylic acid derivatives according to process conditions known per se, characterised in that monophenols having the formula (1) are used as chain terminators in quantities of 0.5 mol % to 8 mol %, preferably 2 mol % to 6 mol %, relative in each case to moles of diphenols, whereby up to 50 mol % thereof, preferably up to 25 mol %, relative in each case to the total quantity of chain terminators, may be replaced by other monophenols.

If the interfacial polycondensation process is used, the chain terminators having formula (1) may be added in solution before, during or after phosgenation. The suitable solvents for dissolving the chain terminators having formula (1) are for example methylene chloride, chlorobenzene or acetonitrile as well as mixtures of these solvents.

The invention also provides the polycarbonates, polyester carbonates and polyesters obtainable by the process according to the invention.

Diphenols for producing the polycarbonates, polyester carbonates and polyesters according to the invention may also be polymers or condensates with phenolic terminal groups, such that polycarbonates or polyester carbonates or polyesters having block structures are also included according to the invention.

The polycarbonates, polyester carbonates and polyesters according to the invention may be worked up by known means and processed to produce thermoplastic molding compositions that may be used for preparing a variety of molded parts by extrusion or injection molding, for example.

These molding compositions may further include other aromatic polycarbonates and/or other aromatic polyester carbonates and/or other aromatic polyesters. Further, the molding compositions may include conventional additives for their art-recognized utility.

Conventional additives for these thermoplastics, such as fillers, UV stabilizers, heat stabilizers, antistatic agents and pigments may also be added to the polycarbonates, polyester carbonates and polyesters according to the invention in the conventional quantities; the demoulding behavior, flow properties and/or flame resistance may optionally also be improved by the addition of external mold release agents, flow control agents and/or flame retardants (e.g. alkyl and aryl phosphites, phosphates, phosphanes, low-molecular carboxylic acid esters, halo compounds, salts, chalk, silica flour, glass and carbon fibers, pigments and combinations thereof. Such compounds are described e.g. in WO99/55772, p. 15–25 and in "Plastics Additives", R. Gächter and H. Müller, Hanser Publishers 1983).

Once processed into molded parts/extrudates of any type, the polycarbonates, polyester carbonates and polyesters according to the invention, optionally blended with other thermoplastics and/or conventional additives, may be used wherever known polycarbonates, polyester carbonates and polyesters are already used. Their range of properties also makes them particularly suitable as substrate materials for optical data storage media such as e.g. CDs, CD-Rs, DVDs or DVD-Rs, but they may also be used for example as films in the electrical sector, as moldings in vehicle construction and as sheets for covers in the safety sector. Other possible applications for the polycarbonates according to the invention are:

1. Safety glass, which is known to be needed in many areas of buildings, vehicles and aircraft, and as visors for helmets.
2. Production of blow moldings (see e.g. U.S. Pat. No. 2 964 794).
3. Production of translucent sheets, in particular twin-wall sheets, for example for covering buildings such as stations, greenhouses and lighting installations.
4. For producing traffic light housings or road signs.
5. For producing foams (see e.g. DE-A 1 031 507).
6. For producing threads and wires (see e.g. DE-A 1 137 167 and DE-A 1 785 137).
7. As translucent plastics containing glass fibres for lighting applications (see e.g. DE-A 1 554 020).
8. For producing precision injection moldings, such as e.g. lens holders. Glass fibers optionally also containing around 1–10 wt. % $MoS_2$, relative to the total weight, are used here.
9. For producing optical device components, in particular lenses for photographic and film cameras (see e.g. DE-A 2 701 173).
10. As light carriers, in particular as optical cables (see e.g. EP-A 0 089 801).
11. As electrical insulating materials for electrical cables and for connector shells and plug-type connectors.
12. As supports for organic light-dependent resistors.
13. For producing lamps, e.g. headlamps or diffusers.
14. For medical applications, e.g. oxygenators, dialysis machines.
15. For food applications, such as e.g. bottles, crockery and chocolate molds.
16. For applications in the automotive sector, e.g. in areas in contact with fuels and lubricants.
17. For sports articles, such as e.g. slalom poles.
18. For household goods such as e.g. kitchen sinks and letterboxes.
19. For housings, such as e.g. electrical distribution cabinets.
20. Production of plastic films, particularly ski-foils.
21. Production of optical data storage.
22. Production of cellular phone housings with improved resistance against perfume, aftershave and skin perspiration.
23. Network interface devices.
24. Transparent washing machines—washing machine doors with improved resistance against detergent solution.
25. Goggles, optical lenses for glasses.
26. Lamp housings for kitchen equipment with improved resistance against cooking vapor or oil vapor.
27 Packaging foils for pharmaceuticals.
28. Chip-boxes and chip.
29. For other applications, such as e.g. stable doors or animal cages.

This application also provides the molded parts and extrudates produced from the polymers according to the invention.

EXAMPLES

Example 1

Preparation of 1,3-bis(tert.-butyl dimethylsilyl)-5-(tert.-butyl dimethyl siloxy) isophthalate 41.9 g (0.23 mol) 5-hydroxyisophthalic acid and 94.0 g (1.38 mol) imidazole are dissolved in 400 ml N,N-dimethyl formamide under an argon atmosphere in a flask topped with a reflux condenser. A solution of 139.8 g (0.932 mol) tert.-butyl dimethyl silyl chloride in 765 ml N,N-dimethyl formamide is added dropwise to this solution. This mixture is heated to 57° C. After 11.5 hours the reaction is cooled and the precipitated crystals isolated and dissolved in n-hexane. The residual tert.-butyl dimethyl silyl chloride is hydrolysed with 0.5 M NaOH. The solution is washed with water and dried over magnesium sulfate. After drying under high vacuum a white solid remains (100.7 g, 83.4%).

$^1$H-NMR (400 MHz, CDCl$_3$) δ=8.26 (s, 1H), 7.70 (s, 2H), 1.03 (s, 18H), 0.99 (s, 9H), 0.39 (s, 12H), 0.12 (s, 6H).

Example 2
Preparation of 5-(tert.-butyl dimethyl siloxy) isophthalic acid 100.7 g (0.191 mol) 1,3-bis(tert.-butyl dimethyl silyl)-5-(tert.-butyl dimethyl siloxy) isophthalate are dissolved in a mixture of 400 ml THF, 1200 ml glacial acetic acid and 400 ml water in a 4-liter flask. The solution is stirred for 3 hours. The solution is diluted with water and cooled to 0° C., whereupon crystals are precipitated. These are removed by filtration and dried under high vacuum (43.6 g, 77.0%).

$^1$H-NMR (400 MHz, CDCl$_3$) δ=12.9 (s, 2H), 8.22 (s, 1H), 7.52 (s, 2H), 0.97 (s, 9H), 0.22 (s, 6H).

Example 3
Preparation of 5-(tert.-butyl dimethyl siloxy) isophthalic acid dichloride 43.6 g (0.1471 mol) 5-(tert.-butyl dimethyl siloxy) isophthalic acid are placed under argon in a 1-liter flask topped with a reflux condenser. 335 ml thionyl chloride are added dropwise. The mixture is heated to 75° C. After 10.5 hours the remaining thionyl chloride is removed by distillation under reduced pressure. A brown oil is obtained (7.29 g, 64.1%).

$^1$H-NMR (400 MHz, CDCl$_3$) δ=8.45 (s, 1H), 7.84 (s, 2H), 1.02 (s, 9H), 0.28 (s, 6H).

Example 4
Preparation of 1,3-bis(p-tert.-butyl phenyl)-5-(tert.-butyl dimethyl siloxy) isophthalate 7.88 g (52.5 mmol) p-tert.-butyl phenol, 150 ml dichloromethane and 45 ml pyridine are placed under argon in a 500-ml flask. 7.29 g (21.9 mmol) 5-(tert.-butyl dimethyl siloxy) isophthalic acid dichloride dissolved in 25 ml dichloromethane are slowly dropped into this mixture. The solution is stirred for 6 hours at room temperature. The solution is concentrated to small volume and the residue taken up in dichloromethane. The solution is washed with 200 ml 1 M NaOH, 200 ml 1 M HCl, 400 ml saturated NaCl solution and then once more with water and dried over MgSO$_4$. After removing the solvent under vacuum the product is obtained as a white powder (9.2 g, 55.8%).

$^1$H-NMR (400 MHz, CDCl$_3$) δ=8.44 (s, 1H), 7.79 (s, 2H), 7.35 (d, 4H), 1.23 (s, 18H), 1.18 (s, 9H).

Example 5
Preparation of 1,3-bis(p-tert.-butyl phenyl)-5-hydroxyisophthalate 9.20 g (16.43 mmol) 1,3-bis(p-tert.-butyl phenol)-5-(tert.-butyl dimethyl siloxy) isophthalate, 175 ml acetone and 25 ml 1 M HCl are poured into a 500-ml flask topped with a reflux condenser. The solution is stirred for 9 hours at 50° C. and for 3 days at room temperature. Acetone and water are then removed under vacuum. The residue is dissolved in 400 ml dichloromethane. It is washed with 400 ml NaCl solution and then with 400 ml water. It is dried over MgSO$_4$ and the volatile components removed under vacuum. The crude product is taken up in 25 ml toluene and precipitated out in 500 ml n-hexane. After filtration and drying under high vacuum the product is obtained as a white solid (6.23 g, 85%).

$^1$H-NMR (400 MHz, CDCl$_3$) δ=10.5 (s, 1 H), 7.84 (s, 2H), 7.51 (d, 4H), 7.25 (d, 4H), 1.35 (s, 18H).

Example 6
Preparation of 1,3-dibenzyl-5-(benzyloxy) isophthalate 5.01 g (27.5 mmol) 3-hydroxyisophthalic acid and 16.59 g (120 mmol) potassium carbonate are placed under argon in a flask. 80 ml N,N-dimethyl formamide are added and 16.51 g (96.5 mmol) benzyl bromide added dropwise to this solution at room temperature with stirring. It is then heated to 57° C. and stirred for a further 48 hours at this temperature. The solution is then cooled and poured onto ice. It is extracted with ethyl acetate. The organic phase is washed repeatedly with saturated NaCl solution. The organic phase is dried over magnesium sulphate, filtered, and the solvent removed under vacuum. A white solid re crystallized out of ethyl acetate is obtained (5.2 g, 42%, melting point: 95.7° C.).

$^1$H-NMR (400 MHz, CDCl$_3$) δ=8.36 (s, 1H), 7.85 (s, 2H), 7.5–7.3 (m, 15H), 5.37 (s, 4H), 5.13 (s, 2H).

Example 7
Preparation of 1-benzyl oxyisophthalic acid 4.52 g (0.01 mol) 1,3-dibenzyl-5-(benzyloxy) isophthalate are added to a mixture of 2.81 g (0.05 mol) potassium hydroxide, 33 ml THF and 50 ml methanol, refluxed and stirred for 14 hours. The reaction mixture is then neutralised with dilute hydrochloric acid. It is repeatedly extracted with chloroform. The organic phases are combined and washed a number of times with water. After drying over magnesium sulfate and filtration, the solvent is removed under vacuum. The remaining oil is taken up again in dichloromethane and shaken out with 1 N NaOH. The combined aqueous phases are acidulated with hydrochloric acid (pH=1.5), whereupon a white solid is precipitated out. The product is filtered off and dried under high vacuum (2.05 g, 75%).

$^1$H-NMR (400 MHz, CDCl$_3$) δ=8.22 (s, 1H), 7.78 (s, 2H), 7.45–7.33 (m, 5H), 5.16 (s, 2H).

Example 8
Preparation of 1,3-diphenyl-5-(benzyloxy) isophthalate 1.23 g (5 mmol) 1-benzyloxyisophthalic acid are dissolved in 18.44 g (155 mmol) thionyl chloride and refluxed under argon. On completion of the generation of gas the excess thionyl chloride was distilled off under vacuum. The remaining residue is dissolved in 10 ml dichloromethane and slowly dropped into a mixture of 1.13 g (12 mmol) phenol dissolved in 20 ml dichloromethane and 6 ml pyridine (113 mmol). The reaction mixture is stirred for 24 hours at room temperature. It is extracted once with 50 ml 1 N NaOH and three times with 50 ml saturated NaCl solution. The organic phase is dried over magnesium sulfate, filtered, and the solvent removed under vacuum. The product is dried at 40° C. under high vacuum (1.95 g, 92%).

$^1$H-NMR (400 MHz, CDCl$_3$) δ=8.83 (s, 1H), 8.05 (s, 2H), 7.5–7.2 (m, 15H), 5.21 (s, 2H).

Example 9
Preparation of 1,3-diphenyl-5-hydroxyisophthalate 1.65 g (3.9 mmol) 1,3-diphenyl-5-(benzyloxy) isophthalate are dissolved in 50 ml ethyl acetate. 0.83 g (0.8 mmol) Pd/C (10%) are added to this solution under nitrogen and hydrogen is introduced for 4 hours. The mixture is filtered and the solvent removed under vacuum. A white powder is obtained (1.1 g, 85%).

$^1$H-NMR (400 MHz, CDCl$_3$) δ=10.25–10.15 (s, 1H), 8.33 (s, 1H), 7.83 (s, 2H), 7.45 (m, 4H), 7.31 (m, 2H), 7.25 (m, 4H).

Other phenols in a similar form can be obtained according to examples 1 to 5 and 6 to 9 above:

| Ex. no. | Terminal group | Structure | Comment |
|---|---|---|---|
| 10 | 1,3-bis(isooctyl phenyl)-5-hydroxyisophthalate | 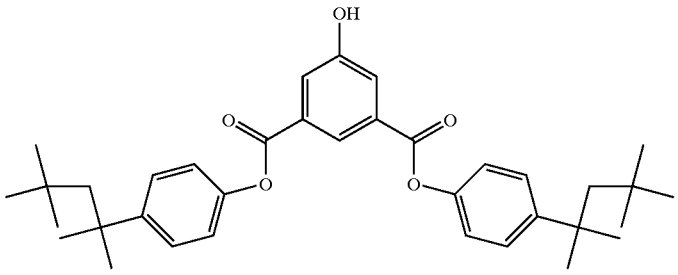 | White solid |
| 11 | 1,3-bis[3,5-di-(tert.-butyl) phenyl]-5-hydroxyisophthalate | 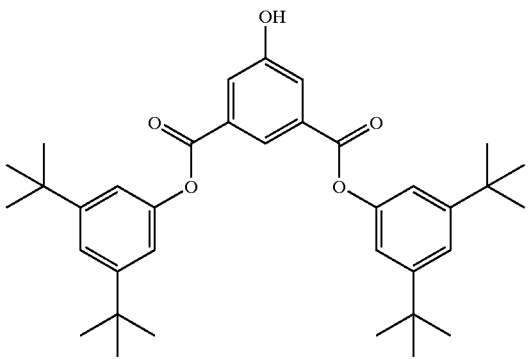 | White solid |
| 12 | 1,3-bis(p-cumyl phenyl)-5-hydroxyisophthalate | 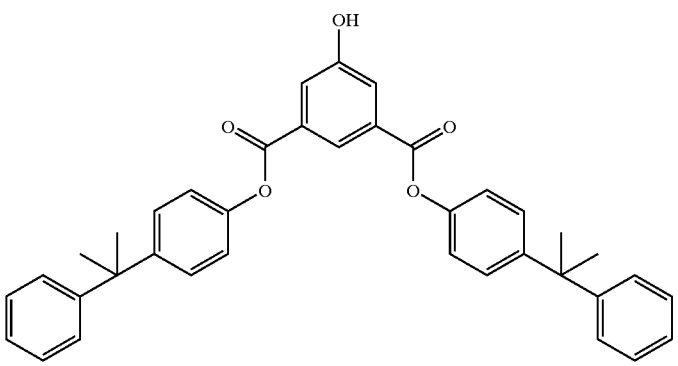 | White solid |
| 13 | 1,3-dicyclodecyl-5-hydroxy isophthalate | 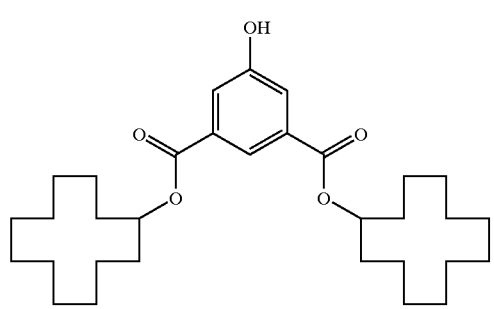 | Oil |

-continued
| Ex. no. | Terminal group | Structure | Comment |
|---|---|---|---|
| 14 | 1,3-dicyclooctyl-5-hydroxy isophthalate | 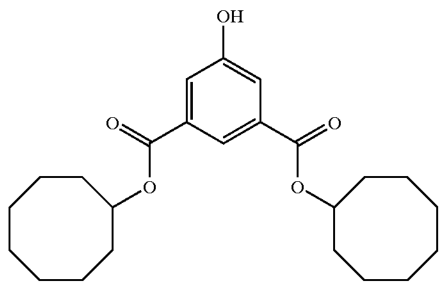 | Oil |
| 15 | 1,3-bis[3,5-(diphenyl oxycarbonyl)phenyl]-5-hydroxy isophthalate | 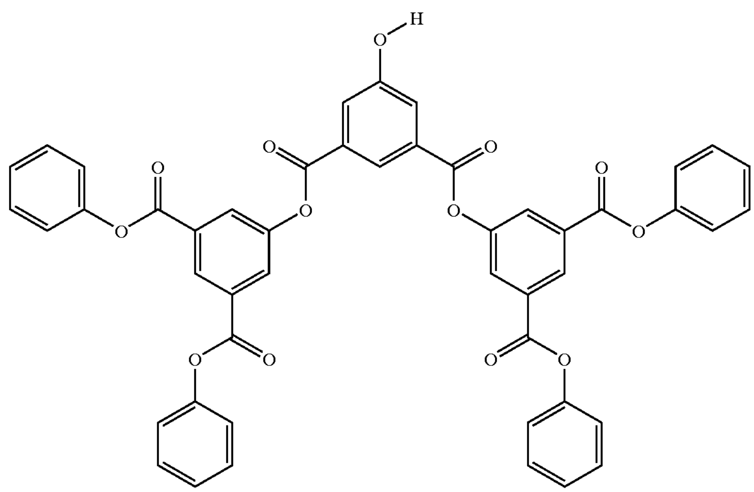 | White solid |
Example 16
3,5-di(4-methyl benzoyl) phenol
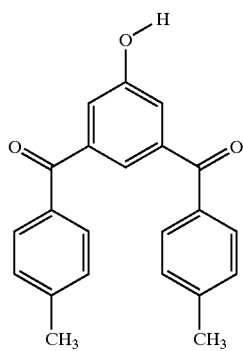
pale yellow solid
Example 17
3,5-di(4-tert.-butyl benzoyl) phenol
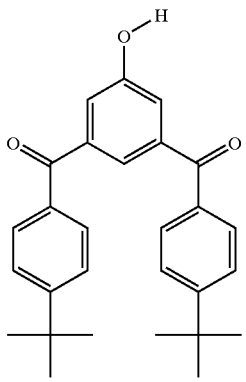
white solid

Example 18
3,5-diphenyl oxyphenol

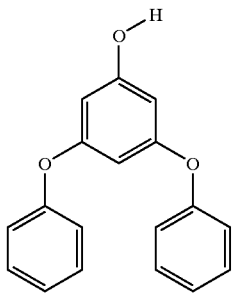

Example 19
Preparation of polycarbonate with branched terminal group 13,698 g (0.06 mol) 2,2-bis(4-hydroxyphenyl) propane and 5,280 g NaOH (220 mol %, relative to bisphenol component) are dissolved in 220 ml water in a flask at room temperature under a nitrogen atmosphere. 1,003 g 1,3-diphenyl-5-hydroxy isophthalate (from Example 9) dissolved in 220 ml dichloromethane are added to this mixture. It is stirred for 15 minutes and then 0.08 ml (1 mol %) N-ethyl piperidine are added to this mixture. 8.3 ml (200 mol %, relative to bisphenol component) phosgene are introduced at room temperature and with vigorous stirring. The pH value is maintained in the range from 12.5 to 13 during this process by making up with dilute NaOH solution. Stirring is continued for a further 30 minutes. It is then diluted with dichloromethane and the organic phase separated off. After acidulating the organic phase with dilute hydrochloric acid it is washed free from electrolytes with water. The polymer dissolved in the organic phase is precipitated in methanol.

Yield: 14.8 g
$M_w$=16240 g/mol
$M_n$=7830 g/mol
D=2.07

Comparative Example 20

The experiment was performed as described in Example 19. Instead of 1,3-diphenyl-5-hydroxyisophthalate, tert.-butyl phenol was used as chain terminator.

$M_w$=16630 g/mol
$M_n$=7920 g/mol
D=2.09

| Polycarbonate | Zero shear-rate viscosity (Pa.s) (at 270° C.) | Molecular weight (g/mol) | Glass transition temperature (° C.) |
| --- | --- | --- | --- |
| Example 19 | 182 | $M_w$ = 16240 $M_n$ = 7830 | 142 |
| Comparative example 20 | 216 | $M_w$ = 16630 $M_n$ = 7920 | 145 |

It can be seen from the table above that with an almost identical molecular weight the polycarbonate according to the invention displays a clearly reduced zero shear-rate viscosity in comparison to a polycarbonate having tert.-butyl phenol as terminal group.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:
1. A phenol having the formula

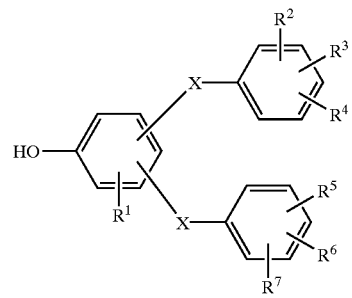

$R^1$, $R^2$, $R^7$ independently one of the others denote H, linear or branched $C_1-C_{18}$ alkyl, Cl, or Br, X is single bond or a divalent radical, $R^3-R^6$ independently one of the others denote H, linear or branched $C_1-C_{18}$ alkyl, cyclic $C_5-C_{18}$ alkyl, phenyl, phenyloxy, phenyl carboxy, benzyl, benzyloxy, naphthyl, naphthyloxy or naphthylcarboxy radicals, excluding bis($C_1-C_{18}$ alkyl phenyl)-4-hydroxyisophthalates, diphenyl hydroxyisophthalate, bis[(diphenyl oxycarbonyl) phenyl] hydroxyisophthalate, diphenyl oxyphenol, 3,5-dibenzoyl phenol, 4-methyl-2,6-dibenzoyl phenol, 2-methyl-4,6-dibenzoyl phenol and 3,5-bis(4-hydroxybenzoyl) phenol.

2. A method of using a phenol conforming to

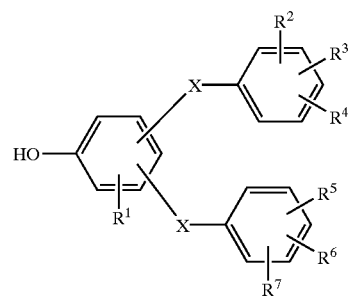

$R^1$, $R^2$, $R^7$ independently one of the others denote H, linear or branched $C_1-C_{18}$ alkyl, Cl, or Br, X is a divalent radical selected from the group consisting of —$CO_2$—, —O—, —$CH_2$— and —CO—, and $R^3-R^6$ independently one of the others denote H, linear or branched $C_1-C_{18}$ alkyl, cyclic $C_5-C_{18}$ alkyl, phenyl, phenyloxy, phenyl carboxy, benzyl, benzyloxy, naphthyl, naphthyloxy or naphthylcarboxy radicals, excluding bis($C_1-C_{18}$ alkyl phenyl)-4-hydroxylsophthalates, diphenyl hydroxyisophthalate, bis[(diphenyl oxycarbonyl) phenyl] hydroxyisophthalate, diphenyl oxyphenol, 3,5-dibenzoyl phenol, 4-methyl-2,6-dibenzoyl phenol, 2-methyl-4,6-dibenzoyl phenol and 3,5-bis(4-hydroxybenzoyl) phenol comprising producing a resin selected from the group consisting of polycarbonate, polyestercarbonate and polyester.

3. A polymeric resin selected from the group consisting of polycarbonate, polyester carbonate and polyester containing at least one structural unit conforming to

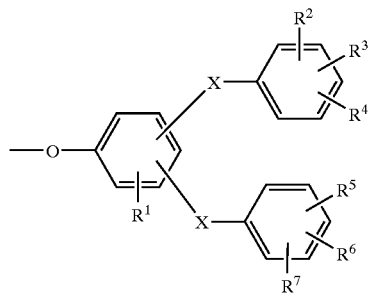

wherein $R^1$, $R^2$, $R^7$ independently one of the others denote H, linear or branched $C_1$–$C_{18}$ alkyl, Cl, or Br, X is a divalent radical selected from the group consisting of —$CO_2$—, —O—, —$CH_2$— and —CO—, and $R^3$–$R^6$ independently one of the others denote H, linear or branched $C_1$–$C_{18}$ alkyl, cyclic $C_5$–$C_{18}$ alkyl, phenyl, phenyloxy, phenyl carboxy, benzyl, benzyloxy, naphthyl, naphthyloxy or naphthylcarboxy radicals, excluding bis($C_1$–$C_{18}$ alkyl phenyl)-4-hydroxyisophthalates, diphenyl hydroxyisophthalate, bis[((diphenyl oxycarbonyl) phenyl] hydroxyisophthalate, diphenyl oxyphenol, 3,5-dibenzoyl phenol, 4-methyl-2,6-dibenzoyl phenol, 2-methyl-4,6-dibenzoyl phenol and 3,5-bis(4-hydroxybenzoyl) phenol.

4. A molded article comprising the thermoplastic molding composition of claim 3.

* * * * *